United States Patent
Flammang

(10) Patent No.: US 6,889,093 B1
(45) Date of Patent: May 3, 2005

(54) ELECTRODE LEAD WITH MULTIPLE BRANCHES

(75) Inventor: Daniel Flammang, Angouleme (FR)

(73) Assignee: Biotronik Mes-und Therpiegeräte GmbH & Co. Ingenieurbüro Berlin, Berlin (DE)

(*) Notice: Subject to any disclaimer, the term of this patent is extended or adjusted under 35 U.S.C. 154(b) by 0 days.

(21) Appl. No.: 09/586,942

(22) Filed: Jun. 2, 2000

(30) Foreign Application Priority Data

Jun. 2, 1999 (DE) .......................................... 199 25 854

(51) Int. Cl.⁷ .................................................. A61N 1/08
(52) U.S. Cl. ...................................................... 607/122
(58) Field of Search .............................. 600/373, 374, 600/375, 393, 509, 515, 519, 377, 381; 607/4, 5, 7, 9, 14, 122, 123, 126, 127; 606/41

(56) References Cited

U.S. PATENT DOCUMENTS

| | | | |
|---|---|---|---|
| 3,866,615 A | | 2/1975 | Hewson |
| 4,664,120 A | * | 5/1987 | Hess .......................... 128/642 |
| 4,726,379 A | * | 2/1988 | Altman et al. ......... 128/419 PG |
| 5,439,485 A | | 8/1995 | Mar et al. ................... 607/119 |
| 5,824,031 A | * | 10/1998 | Cookston et al. ............ 607/122 |
| 5,855,592 A | * | 1/1999 | McGee et al. ................. 607/4 |
| 6,076,012 A | * | 6/2000 | Swanson et al. ............... 604/21 |

FOREIGN PATENT DOCUMENTS

| | | | |
|---|---|---|---|
| DE | 196 26 352 | 1/1998 | |
| EP | 0 426 089 | 5/1991 | |
| EP | 0 479 435 | 4/1992 | |
| EP | 0 538 990 | 4/1993 | |
| EP | 0 601 328 | * 6/1994 | ............ A61N/1/05 |
| EP | 0 602 356 | 6/1994 | |
| WO | WO 94/03233 | 2/1994 | |
| WO | 97/28844 | 8/1997 | |
| WO | WO 97/36639 | 10/1997 | |
| WO | WO 98/11939 | 3/1998 | |

* cited by examiner

*Primary Examiner*—Nicholas D. Lucchesi
*Assistant Examiner*—Frances P. Oropeza
(74) *Attorney, Agent, or Firm*—Venable LLP; Catherine M. Voorhees

(57) ABSTRACT

An electrode arrangement, in particular for the intracardial discharge of defibrillation pulses in the atrium of a heart, comprising an electrode line which in the region of its distal end has a plurality of electrically conductive surface portions as electrodes which can be electrically connected by way of the electrode line to an electrical pulsedischarging device such as defibrillator, wherein the electrode line is adapted to be split in the electrode-bearing region of its distal end into at least two respectively electrode-bearing branches.

13 Claims, 18 Drawing Sheets

ELECTRODE LEAD WITH MULTIPLE BRANCHES

BACKGROUND OF THE INVENTION

The invention concerns an electrode arrangement, in particular for the intracardial discharge of defibrillation pulses in the atrium or the ventricle of a heart, having an electrode line which in the region of its distal end has a plurality of electrically conductive surface portions as electrodes, which can be electrically connected by way of the electrode line to an electrical pulse-discharging device such as a defibrillator, cardioverter or pacemaker or the like.

Certain cardiac palpitations or arrhythmia phenomena, including in particular ventricular and atrial fibrillation, but possibly also accelerating tachycardia phenomena which have not yet passed into the state of fibrillation are electrotherapeutically treated with good prospects of success by applying short-duration electrical pulses or shocks to the sensitive cardiac tissue.

In that situation, in order rapidly to achieve termination of those life-threatening arrhythmia effects with a high level of certainty, relatively high voltages are conventionally applied and high levels of energy are supplied to the cardiac tissue, which in many cases results in tissue damage and serious stresses such as pain for the patient. In addition, in relation to implantable units, the provision of those high voltages and high energy levels requires expensive apparatus implementation with special structural and insulating elements, in particular powerful batteries and capacitors. Finally, electrode arrangements of large area were and still are used for transmitting the cardioversion energy to the cardiac tissue, and the production and implantation thereof involves a high cost level.

The design of cardioverters or defibrillators (hereinafter jointly referred to by the term "cardioverter") and the associated electrode arrangements has been the subject of a drive for increasing perfection. In that respect, on the one hand numerous technical solutions have been proposed for ascertaining and providing, in the best possible differentiated fashion, the energy and voltage required for cardioversion of the specific cardiac arrhythmia phenomena involved as well as advantageous pulse shapes and sequences and on the other hand various electrode arrangements have been proposed, which were each considered advantageous from given respective points of view. In actual fact substantial practical improvements which have promoted the widespread practical use of implanted cardioverters or defibrillators and combined pacemakers/cardioverters have proven successful.

In the course of that development increasingly refined and powerful endocardiac defibrillation electrode lines have been described, which afford considerable advantages in terms of implantation and in regard to the operative risks, see for example WO/A-94/03233, EP-A 0 602 356 or the present applicants' prior application DE 196 26 352.2. The endeavours in that respect are inter alia along the lines of applying a cardioversion shock to larger areas of the cardiac tissue by the provision of a plurality of and/or large-area electrode on an endocardiac line, thereby to approximate the area of action of endocardiac electrode arrangements to that of subcutaneous or epicardiac surface electrodes.

With that background of the state of the art in mind, the object of the present invention is that of providing an electrode arrangement which permits advantageous defibrillation.

SUMMARY OF THE INVENTION

In accordance with the invention that object is attained by an electrode arrangement of the kind set forth in the opening part of this specification, in which the electrode line in the electrode-bearing region of its distal end is adapted to be split into at least two branches respectively carrying electrodes. Preferably for that purpose the electrode line has splitting means in the electrode-carrying region at the distal end of the electrode line, which splitting means are adapted to split up the electrode-bearing region and are connected to actuating means which are arranged at the proximal end of the electrode line.

The capability of the distal end of the electrode line being split up in that way affords a series of advantageous options, both in terms of therapy and also diagnosis, insofar as the electrode can be positioned for example at various laterally displaced locations of the heart without two separate electrode lines being required for that purpose. In that connection, a particularly preferred electrode arrangement is one in which the electrode-bearing region has a shaping structure in at least one of the branches, which is activatable simultaneously with or after splitting, and which is of such a nature that a first of the branches assumes a shape as a septal branch and a second branch assumes a shape as a lateral branch for assuming a septal position and a lateral position respectively in the atrium or the ventricle of a heart so that the septal branch and the lateral branch bear at least in a region-wise manner against the septal wall and the lateral wall respectively of the atrium or the ventricle.

Such an arrangement makes it possible for electrodes to be positioned on mutually oppositely disposed side walls of the heart and for them to be actuated for example in bipolar mode in such a way that the others of the oppositely disposed electrodes which are associated with each other in pairs can serve as an anode and a cathode for the discharge of voltage pulses to the myocardium (cardiac tissue) of the atrium. An electrode arrangement of that kind stimulates in particular a layer of the myocardium/which is defined by the two electrodes.

In an alternative embodiment of such an electrode arrangement the electrode-bearing branches have resilient structures as a shaping structure or splitting means, which are pre-shaped in such a way that by virtue of spring forces they cause the electrode-bearing branches to split up. The actuating means can then include a sliding sleeve which extends over the electrode line as far as the distal end thereof or into the proximity thereof and which at the proximal end of the electrode line has engagement means for displacing the sliding sleeve in the longitudinal direction of the electrode line. The sliding sleeve embraces the electrode-bearing branches at the distal end of the electrode line and holds them close together with the spring structure in a stressed condition. In that state the electrode line can be introduced for example into the atrium or the ventricle of a heart. The sliding sleeve is then retracted in the longitudinal direction of the electrode line and releases the electrode-bearing regions. The spring means of the electrode-bearing regions then cause the distal end of the electrode line to spread open into the individual branches. That then affords an electrode line whose electrode-bearing branches at the distal end are preferably in a shape such that one of the branches assumes a lateral position in the atrium of a heart and a second of the branches assumes a rectal position. An electrode shape of that kind permits timely and effective defibrillation even with weaker currents than were hitherto usual so that the defibrillation procedure involves a lower pain level for the patient.

A preferred electrode arrangement is one whose shaping structure has a memory metal structure in at least one of the branches, which is of such a nature that it involves a predetermined change in shape which can be triggered off by an event such as a change in temperature, so that the result after the change in shape is the preferred shape which makes it possible for the branches, which are inserted into the atrium of a heart, of the distal end of the electrode line to bear against the walls of the atrium in the described manner. The memory metal structure preferably contains titanium and corresponds to the known memory metal structures which by virtue of their crystal structure are suitable for abruptly altering their shape, for example in the event of a change in temperature. For triggering off that change in shape, it is preferably possible to fit into the branches of the distal end of the electrode line, electrical heating elements which can be connected to a current source at the proximal end of the electrode line so that the change in shape can be triggered off by connecting the electrical heating elements to the current source.

In a preferred embodiment the branches of the electrode line are respectively provided with an equal number of electrodes, wherein each electrode of a branch is unambiguously associated with an electrode of the other branch. Preferably each branch bears five to seven electrodes. With an arrangement of that kind, it is possible to produce five to seven of the layers which have already been referred to above and which are each defined by the respective mutually associated electrodes and in which the myocardium of the atrium can be stimulated.

A particularly preferred electrode arrangement is one in which the electrode-bearing region in the distal end of the electrode line can be split into two branches which are respectively provided with equidistantly arranged electrodes, wherein each electrode of a branch is associated in pairs with an electrode of the other branch, for the discharge of bipolar pulses. This alternative embodiment of the electrode arrangement is based on the realisation that two electrodes which are associated with each other in pairs are already sufficient to define a layer in the atrium of the heart and to stimulate same by the discharge of a voltage pulse in a bipolar mode of operation between the two electrodes serving as an anode and a cathode.

A particularly preferred electrode arrangement is one in which the electrodes are arranged on the lateral and septal branches in such a way that in the atrium of a heart they assume such positions that each two electrodes which are associated with each other in pairs make it possible to produce defined layers, starting from the transition of the vena cava of the heart into the atrium thereof, thereby subdividing the atrium, in parallel successive relationship.

Such an arrangement of the electrodes is attained if section lines extending parallel to each other are laid through the atrium of a heart at a spacing of for example a centimeter and electrodes are provided at the points of intersection of those notional section surfaces with the branches of the electrode line, which bear against the walls of the atrium.

After an element arrangement of that kind has been introduced into the atrium of a heart, such an electrode arrangement makes it possible for the atrium to be stimulated either successively in time-displaced relationship in a cascade-like procedure or simultaneously with bipolar voltage pulses, and in that way makes it possible to achieve a defibrillation effect with an extremely low level of stimulation energy. That affords the great advantage that defibrillation can be substantially pain-free for the patient.

The electrodes are preferably separately actuable and such that they are suitable both for receiving electrical signals from the heart and also for delivering electrical pulses to the heart. An electrode arrangement of that kind makes it possible to generate a large number of stimulation patterns but also to detect a large number of signals and symptoms which can be put to use for accurately determining the optimum stimulation pattern.

The electrodes are preferably in the form of ring or tip electrodes. In addition the electrodes of a branch are preferably at a respective spacing of about one centimeter from the adjacent electrode or the adjacent electrodes.

Preferably, in addition to the two or more branches already referred to above, the electrode arrangement has at least one further branch which is designed to assume a position in the ventricle or the atrium, respectively of heart and which has at least one electrode. An electrode arrangement of that kind increases the number of diagnostic and therapeutic options insofar as the ventricle and atrium electrodes can be combined with each individual one or any combination of the other electrodes.

BRIEF DESCRIPTION OF THE DRAWINGS

The invention will now be described in greater detail by means of embodiments with reference to the accompanying drawings in which.

DETAILED DESCRIPTION OF THE INVENTION

Figure 1A:
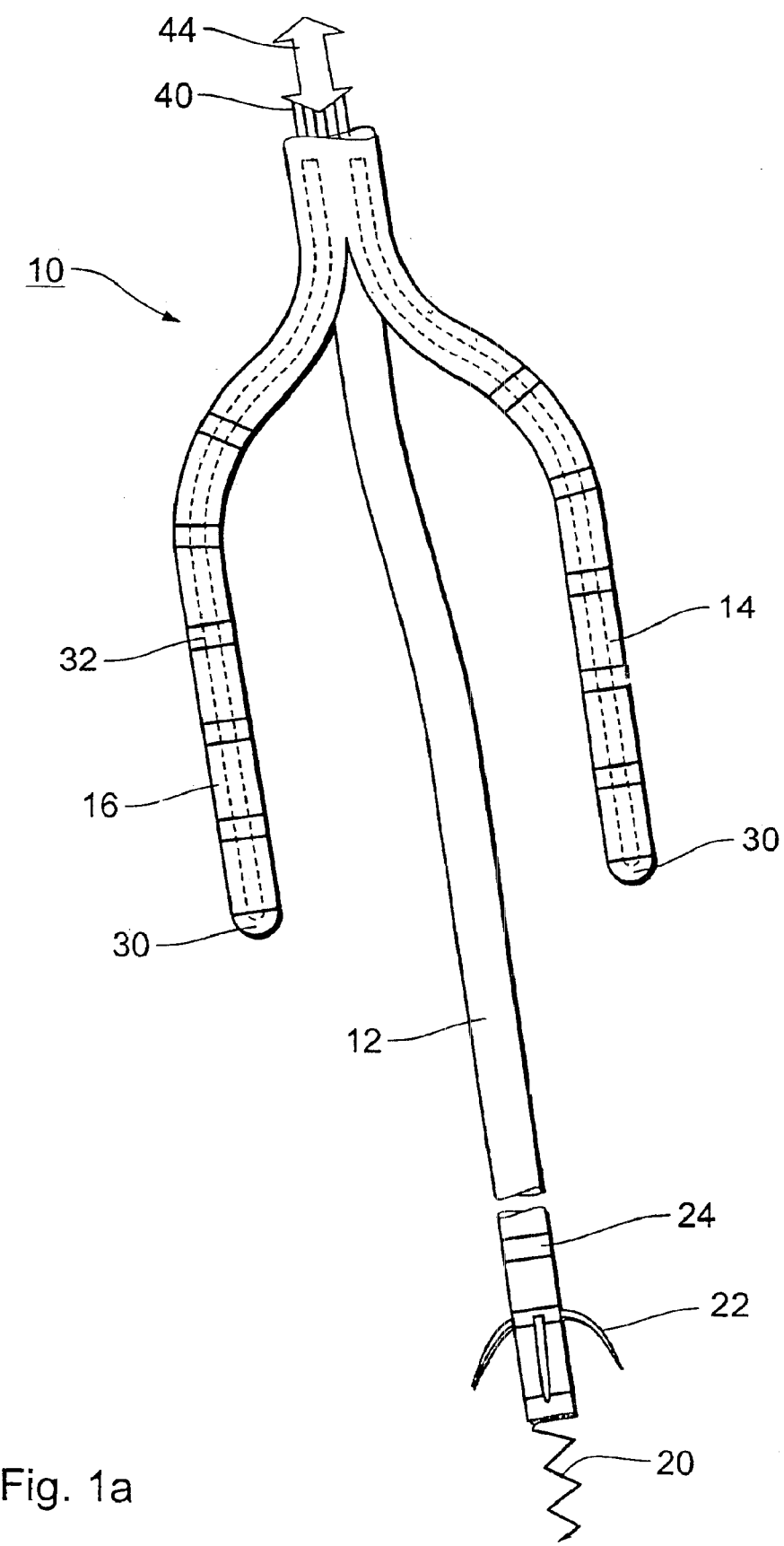
FIGS. 1a to d show the distal end of four alternative embodiments of an electrode line with an electrode arrangement according to the invention.

The distal end of an electrode line 10, as shown in FIG. 1, is split up into three branches, more specifically a ventricular branch 12, a septal branch 14 and a lateral branch 16.

The septal branch 14 and the lateral branch 16 each have six electrodes which are arranged equidistantly relative to each other and which are formed by conductive surface portions of the branches 14 and 16. The electrodes arranged at the free end of the two branches are in the form of tip electrodes 30 while the other electrodes which respectively follow the tip electrodes and in successive relationship with each other at a spacing of about one centimeter are in the form of ring electrodes 32. Each of the electrodes 30 and 32 can be individually connected by way of suitable signal and control lines 40 to a device for receiving electrical signals and for delivering voltage pulses with a defibrillator (not shown). Further-more, at the distal end of both the lateral and the septal branch 14 and 16 there may be provided radiologic markers 34 for facilitating the positioning of the electrode line as well as for controlling the position by means of radiology.

At its free end the ventricular branch 12 has a screwing-in tip 20 for anchoring in the myocardium or heart tissue, and spacers 22 in order to hold the free end of the ventricular branch 20 at a predetermined spacing relative to the myocardium or heart tissue. In addition the ventricular branch 12 of the electrode line 10, as shown in FIG. 1a, is provided with a ring electrode which serves as a ventricle electrode 24. The screwing-in tip 20 may bear one or more radiologic markers 28.

Figure 1B:
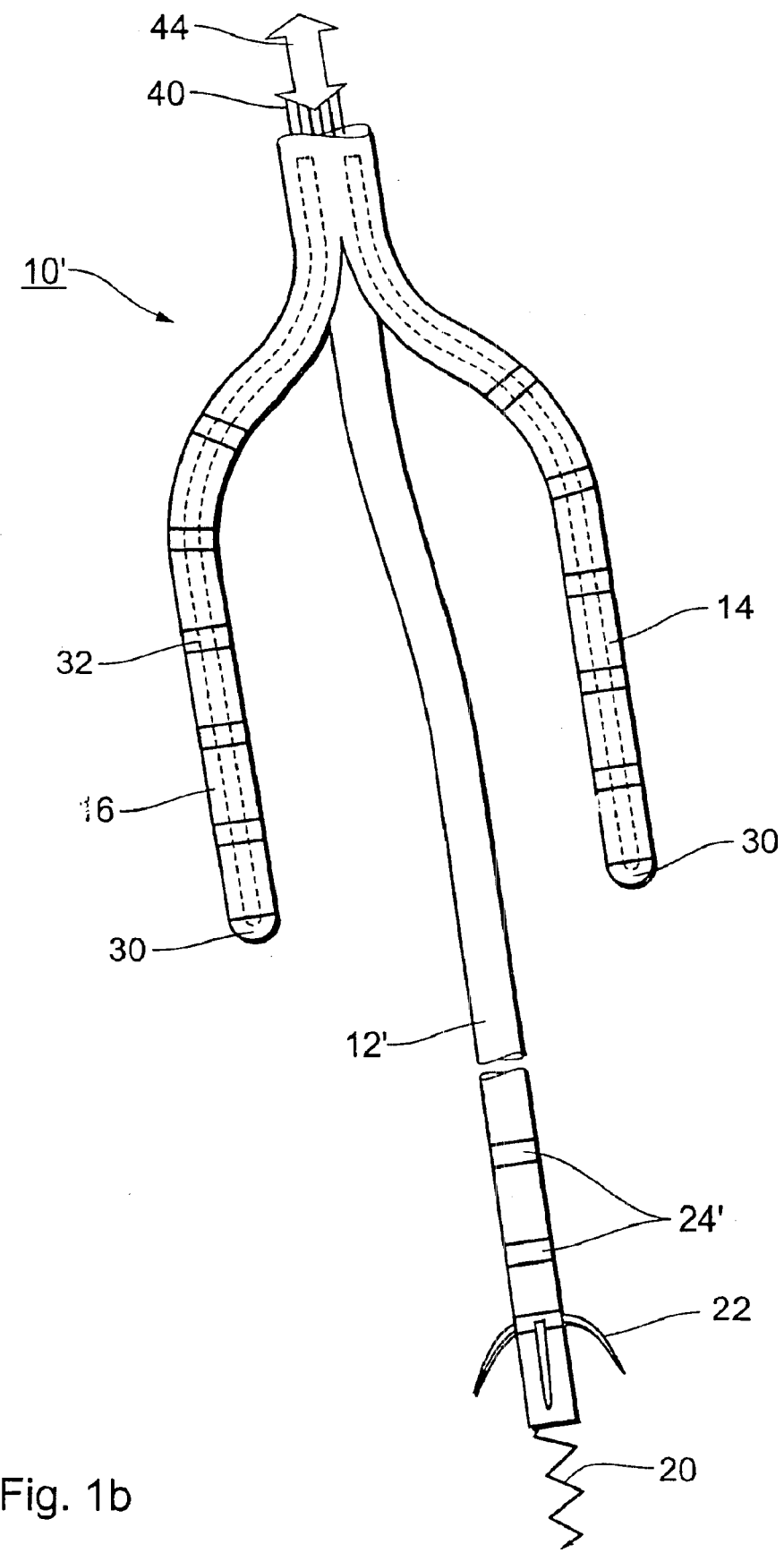

As shown in FIG. 1b, the ventricular branch 12' of the electrode line 10' may bear two distal ring electrodes 24' for sensing and pacing the right ventricle in a standard manner. The two distal ring electrodes 24' could also serve as ventricle electrodes for bipolar or unipolar stimulation of the ventricle alternatively.

Figure 1C:
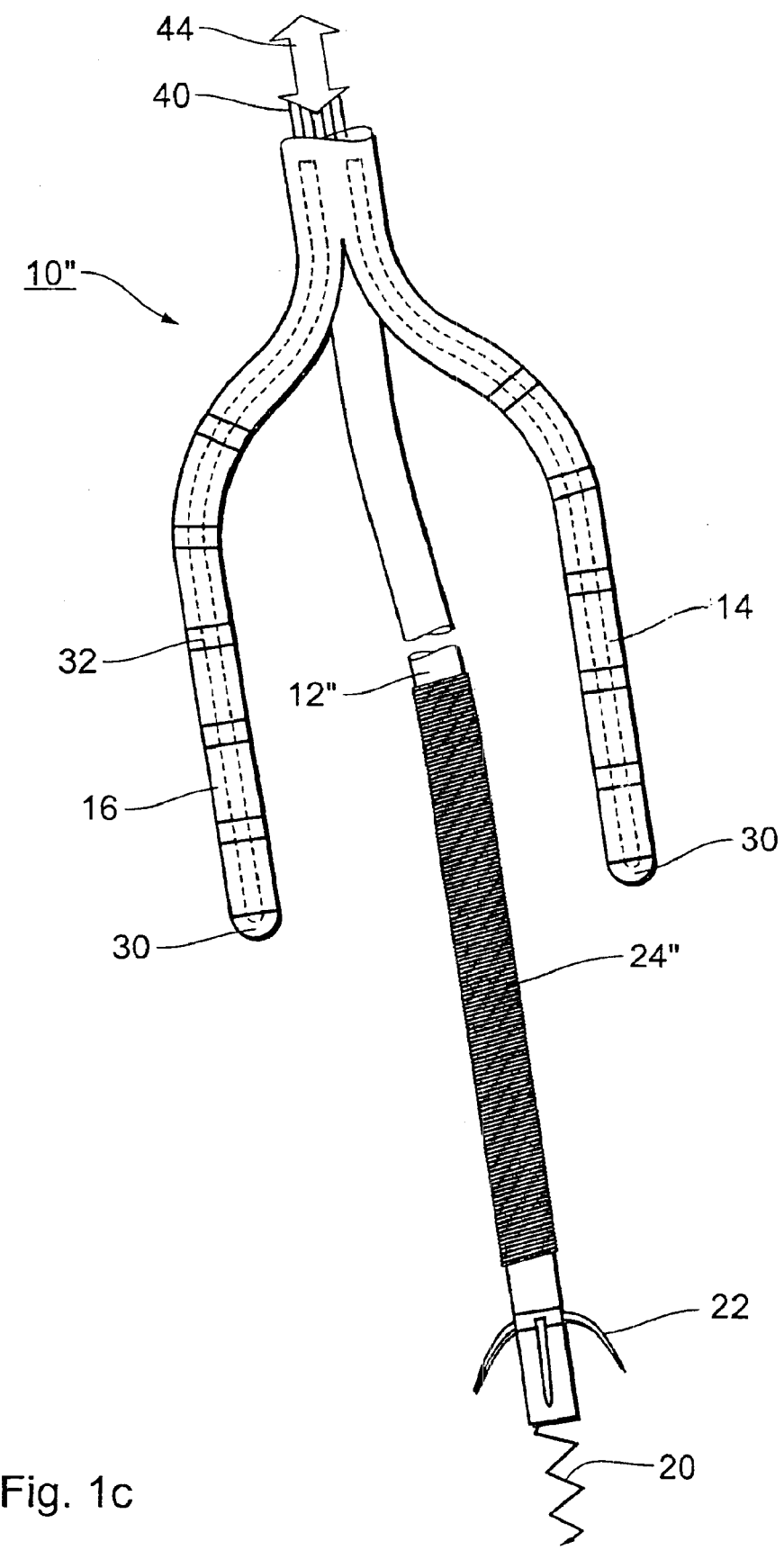

In an alternative embodiment the ventricular branch 12" of the electrode line 10", as shown in FIG. 1c, is equipped with an unique defibrillatory coil electrode 24" about 6 cm in length as usually designed for standard ventricular defibrillatory systems.

Figure 1D:
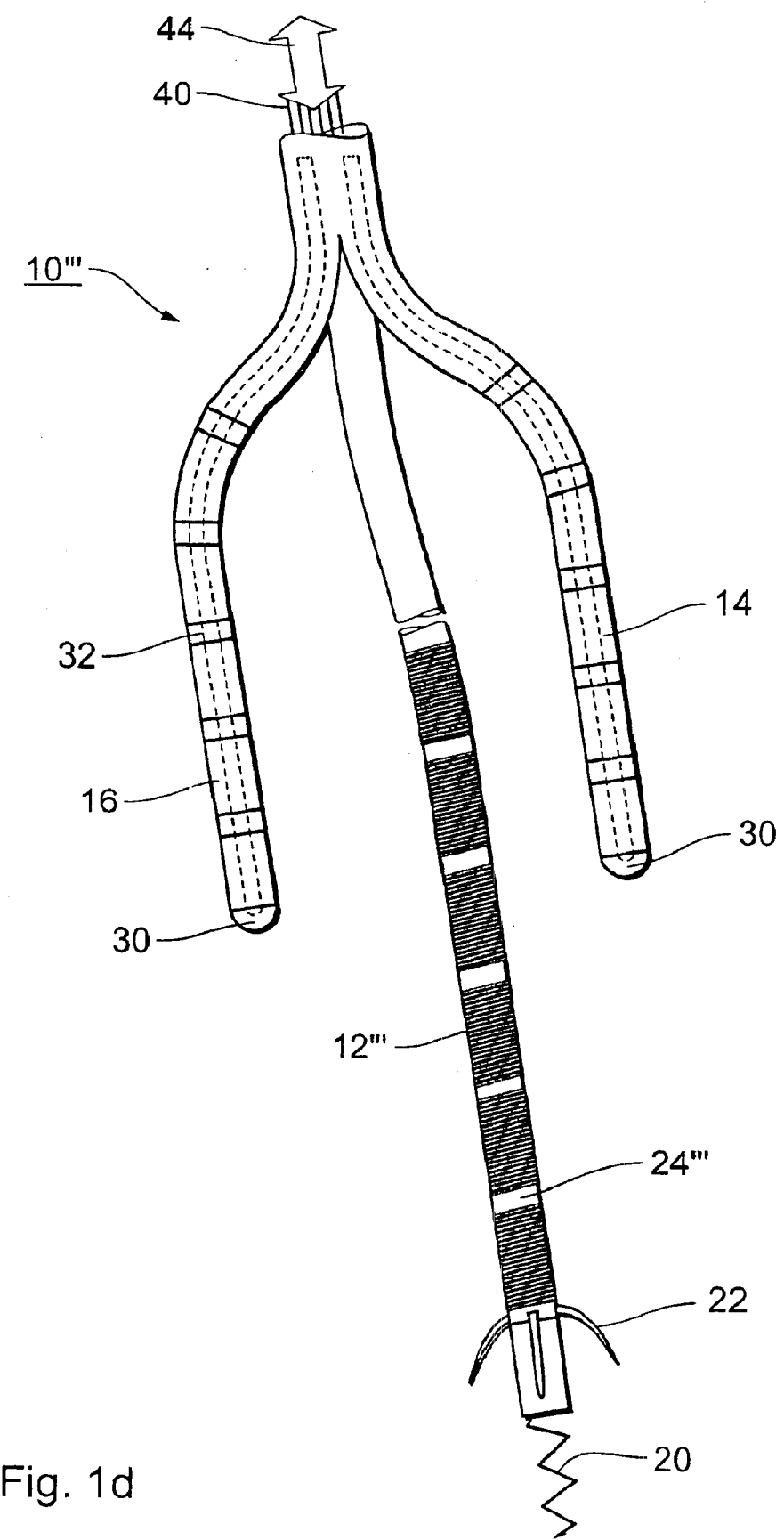

In yet another preferred embodiment of the electrode line 10''', as shown in FIG. 1d, the distal end of the ventricular branch 12''' is bearing 6 separate small coils 24''', each of them 8 mm in length and being spaced apart from each other by plastic joining and insulation material 2 mm in length.

Figure 2A:
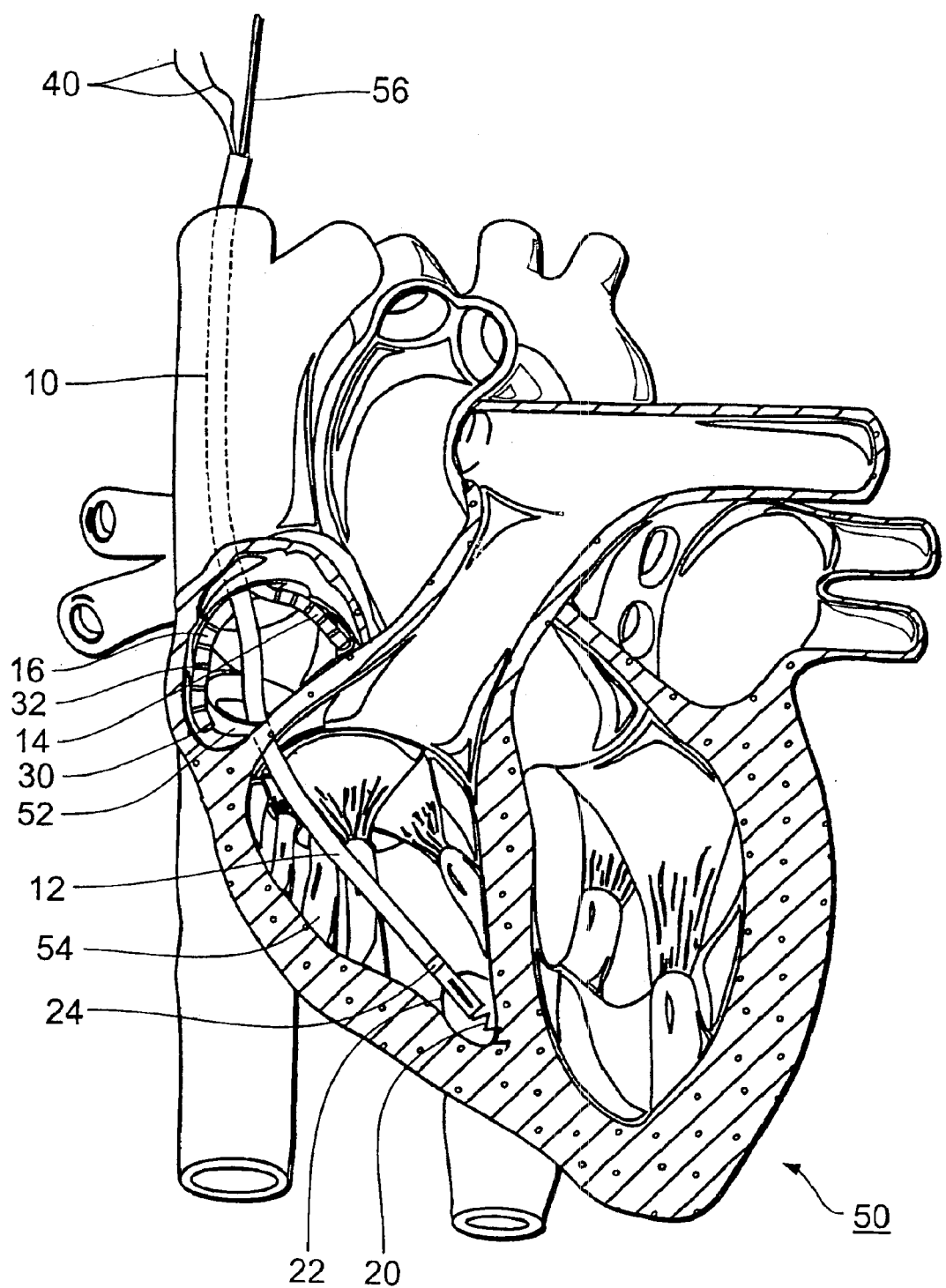
FIGS. 2a and b show an electrode line as illustrated in FIG. 1a inserted into a human heart, in different scales.

FIGS. 2a and b show the electrode arrangement illustrated in FIG. 1a after it has been inserted into a human heart 50, more specifically into its right atrium 52 and its right ventricle 54. The ventricular branch 12 extends into the ventricle 54 of the heart 50. The distal end of the ventricular branch 12 is fixed in the myocardium by way of the screw-in tip 20 and is held at a predetermined spacing relative to the myocardium by way of the spacers 22.

The septal branch 14 and the lateral branch 16 bear against the walls of the atrium 52, more specifically the septal branch 14 against the inner wall of the atrium, which is towards the septum, and the lateral branch against the outer side wall of the atrium 52.

Figure 2B:
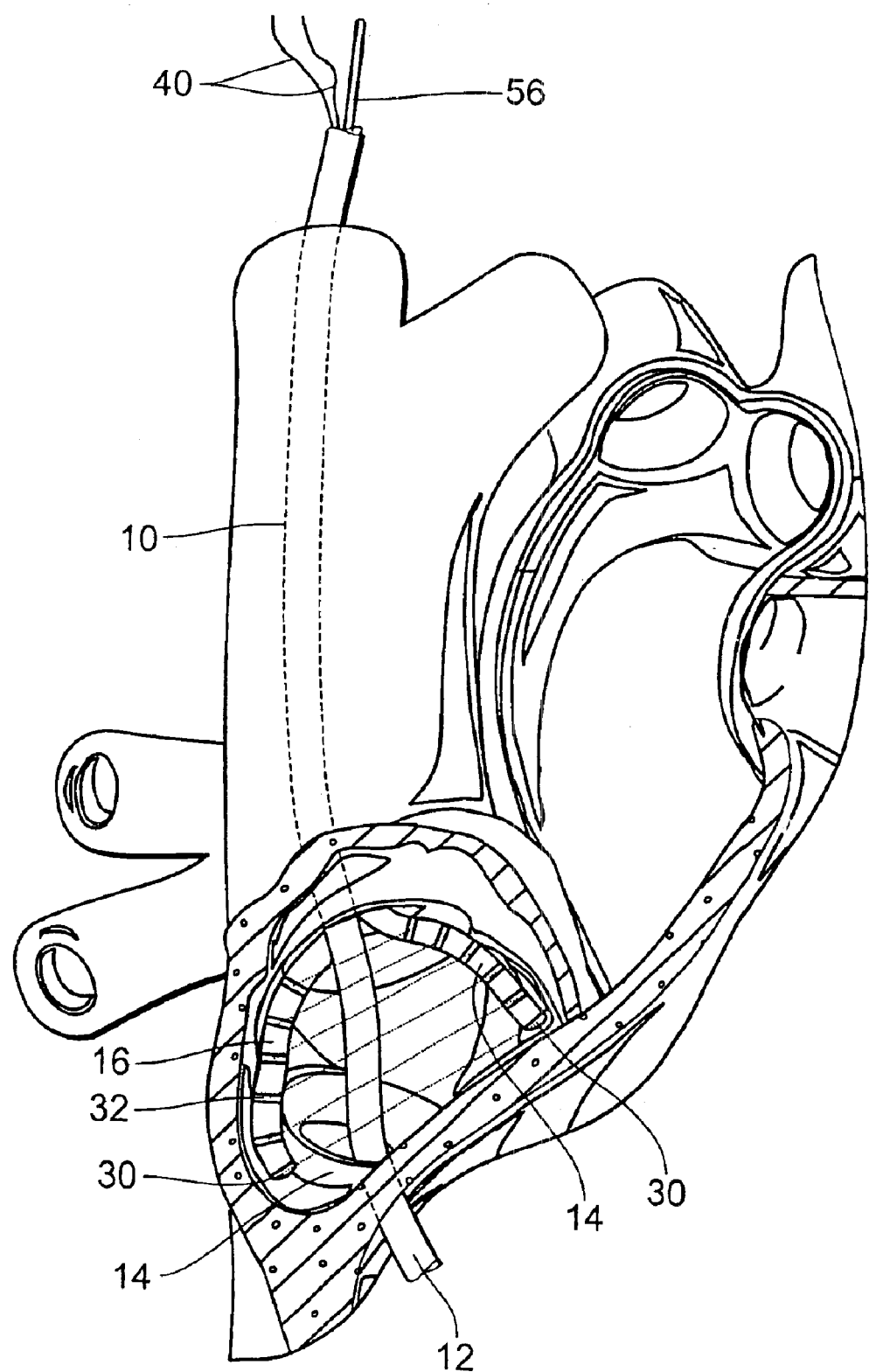

As can be seen from FIG. 2b the electrode 30 and 32 of the septal and the lateral branches 14 and 16 bear against the side walls of the atrium. The tip electrodes of the two branches 14 and 16 and the respectively following ring electrodes 32 are respectively associated in pairs with their counterpart in the respective other branch 14 or 16. In that way the electrodes 30 and 32 respectively form bipoles which are arranged in substantially mutually parallel relationship and which define six layers which subdivide the atrium 54 into five identical slices, each of which is one centimeter high, beginning at the transition of the upper vena cava 56 to the atrium 52 and from there extending inclinedly downwardly about five centimeters. Dash-dotted lines mark the layers which are defined by the electrode pairs.

Figure 3A:
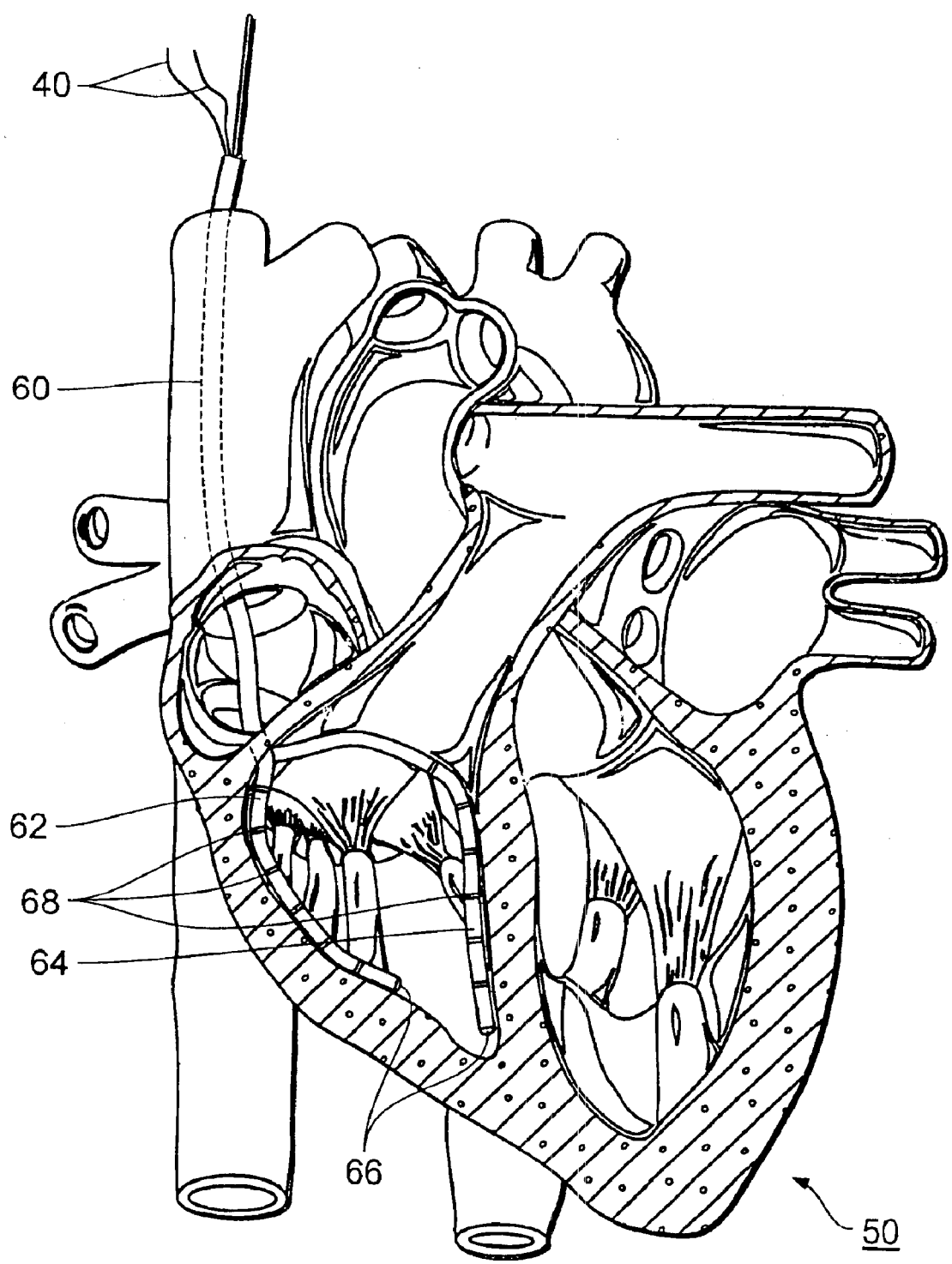
FIG. 3a–c Show alternative embodiments of an electrode line inserted into a human heart.
Figure 3B:
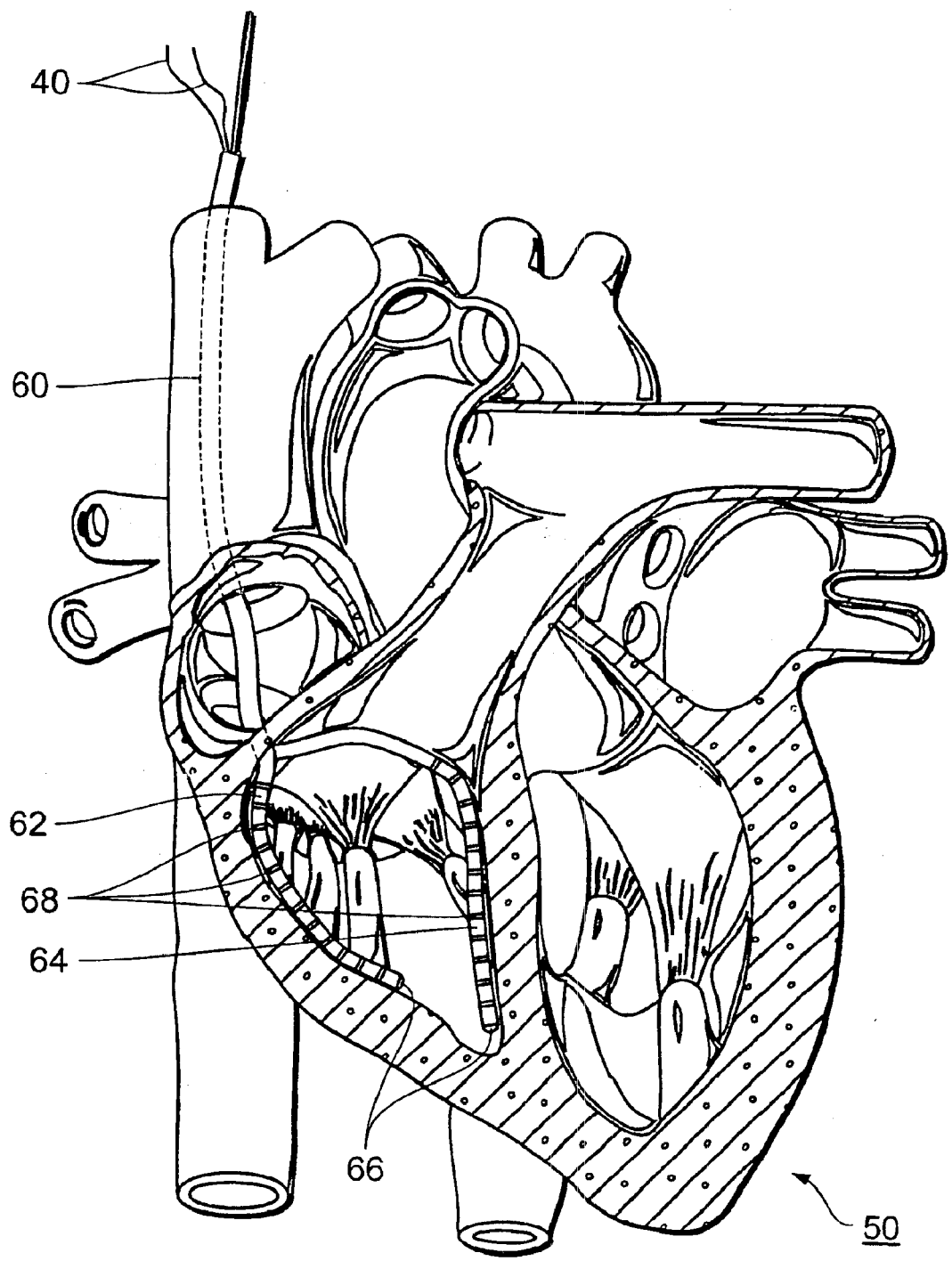
Figure 3C:
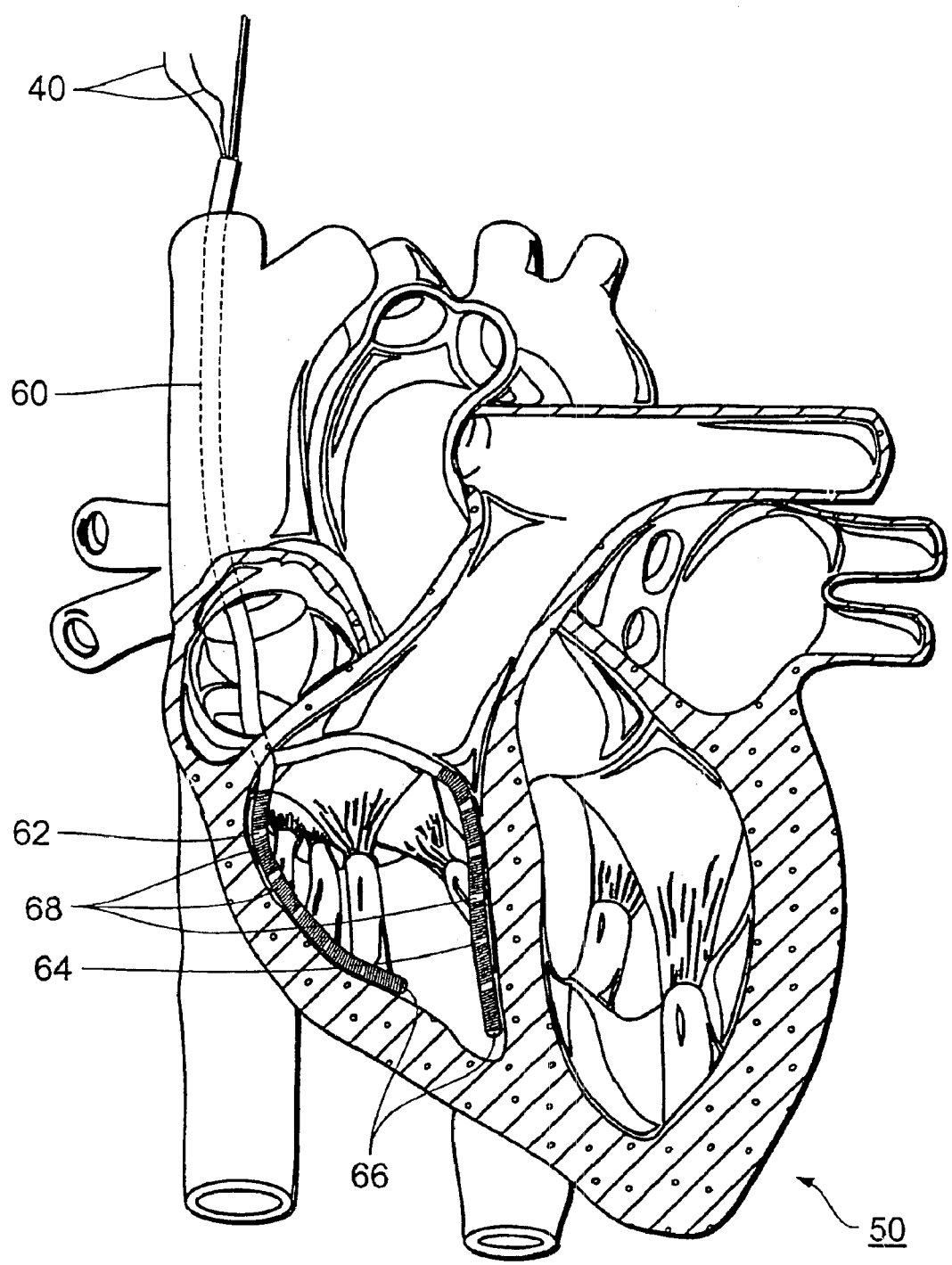

In alternative embodiments, as shown in FIGS. 3a to 3c, the distal end of an electrode line 60, as shown in FIG. 1, is split up into two ventricular branches 62 and 64, more specifically a septal ventricular branch 62 and a lateral ventricular branch 64. The septal branch 62 is formed so that the septal branch bears at least in a region-wise manner against the septal wall whereas the lateral branch bears at least in a region-wise manner against the lateral wall of the ventricle.

Both, the septal branch 62 and the lateral branch 64 may each be provided with different electrode configurations.

The septal and lateral branches 62 and 64 of the embodiment shown in FIG. 3a each have six electrodes which are arranged equidistantly spaced by 7 to 8 mm relative to each other and which are formed by 2 to 3 mm long conductive surface portions of the branches 62 and 64. The electrodes arranged at the free end of the two branches are in the form of tip electrodes 66 while the other electrodes which respectively follow the tip electrodes and in successive relationship with each other at a spacing of about one centimeter are in the form of ring electrodes 68. Each of the electrodes 66 and 68 can be individually connected by way of suitable signal and control lines 40 to a device for receiving electrical signals and for delivering voltage pulses with a cardioverter (not shown).

In an alternative embodiment, lateral and septal branches 62 and 64 each may bear 12 ring electrodes 68' having a length of 2 mm and being equally spaced apart from each other by 4 mm plastic transition zones 70'; see FIG. 3b.

In another preferred embodiment small coils tiered electrodes 68" are provided on both the lateral and the septal branch 62 and 64. Each coil 68' has covers a length of 8 mm. The coils are equally spaced apart from each other by plastic transition zones 70' having a length of 2 mm.

FIGS. 2a and 3 additionally show an adjusting wire 56 which is guided in the electrode line 10 and which serves for angular adjustment of the spacers 22 and thus for adjustment of the myocardium spacing of the electrode 24.

Figure 4:
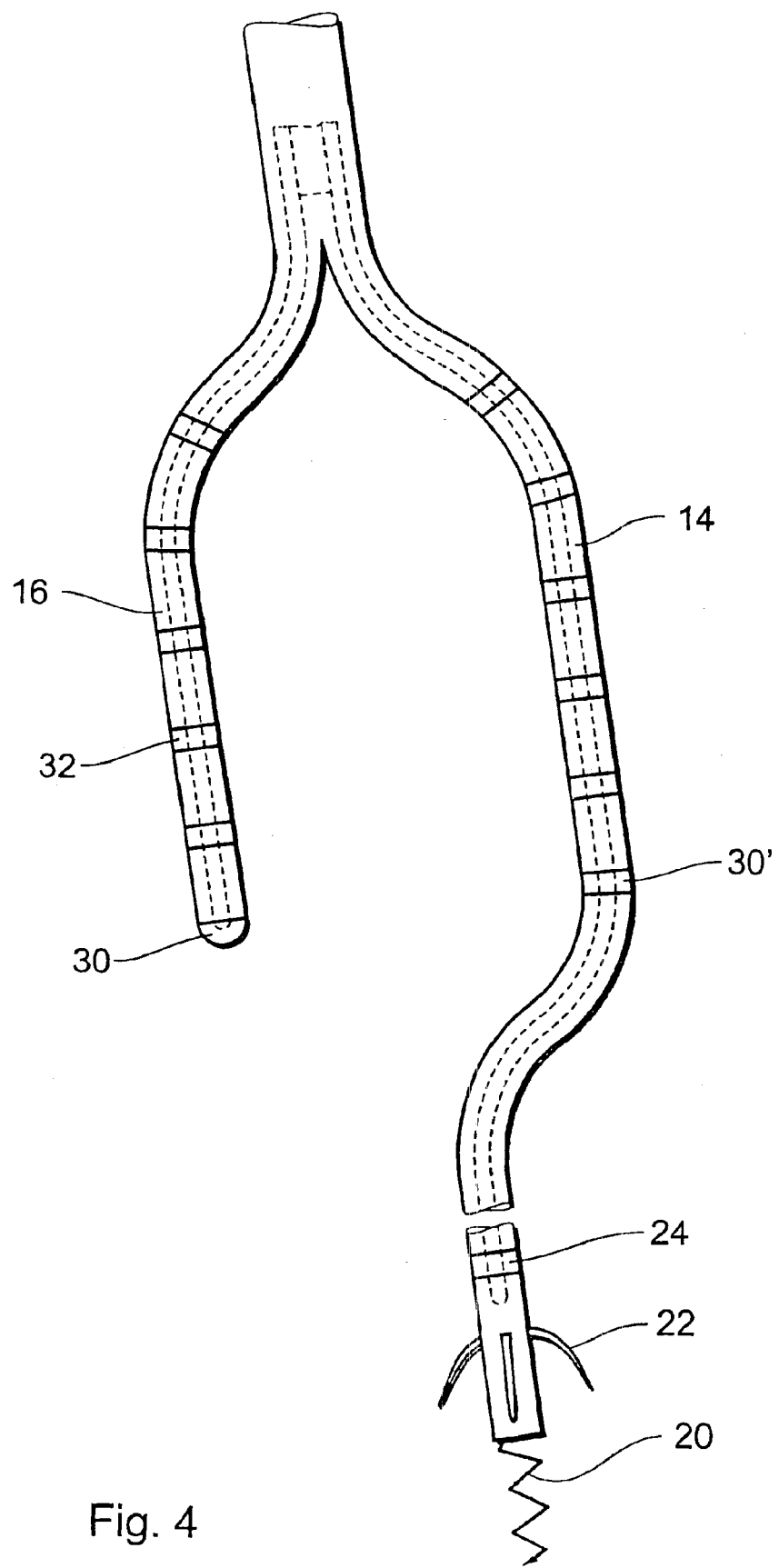
FIG. 4 shows an alternative embodiment of the electrode arrangement illustrated in FIG. 1.

FIG. 4 shows an alternative form of the configuration illustrated in FIGS. 1 and 2 of the distal end of the electrode line. In the case of the electrode line 10 illustrated in FIG. 4, the lateral branch 16 is of precisely the same nature as in FIGS. 1 to 3. The septal branch 14' however is extended and goes directly into the ventricular branch 12. In order to achieve a similar configuration with the electrode arrangement shown in FIG. 4 to that involved in the arrangement illustrated in FIGS. 1 to 3, the septal branch 14', instead of a tip electrode, has a further ring electrode 32'. In other respects the arrangement of the electrodes 30' and 32' which are intended to be positioned in the atrium is substantially the same as in the arrangement shown in FIG. 1.

Figure 5A:
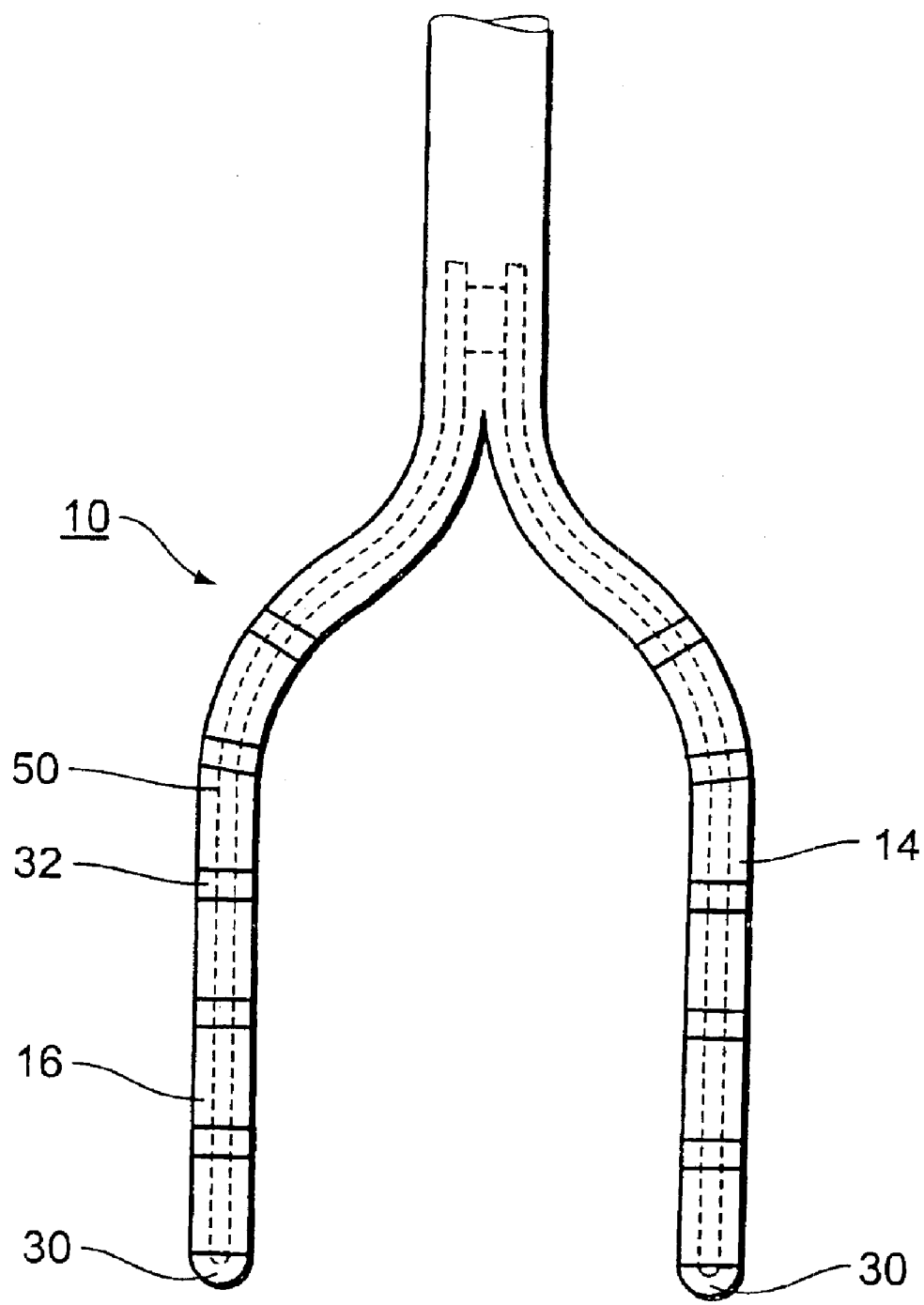
FIGS. 5a to c show three further alternative embodiments of the electrode arrangement without ventricle electrode.

FIG. 5a shows a simplified electrode line 10" which does not have a ventricular branch and which in other respects corresponds to the electrode arrangement shown in FIGS. 1 to 3.

Figure 6A:
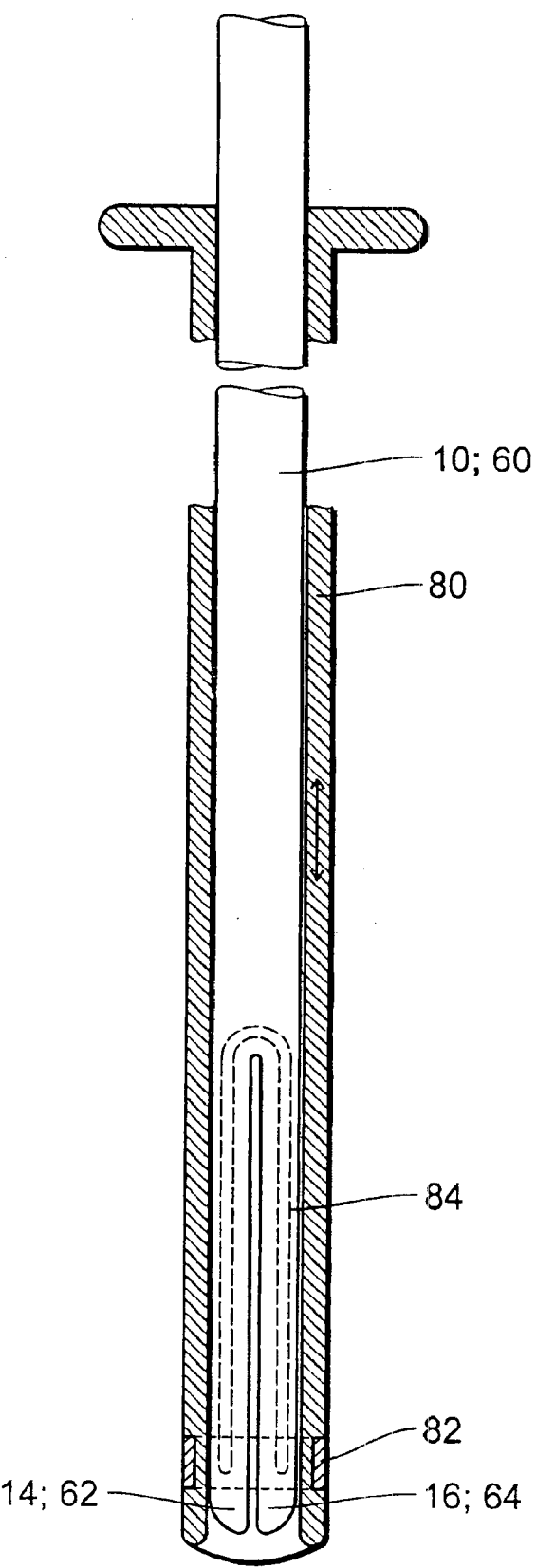
FIGS. 6a to d are diagrammatic views of an insertion catheter for an electrode line mechanical comprising means for splitting up the distal end thereof and FIG. 7 is a diagrammatic view of alternative means for splitting up the distal end of the electrode line.
Figure 6B:
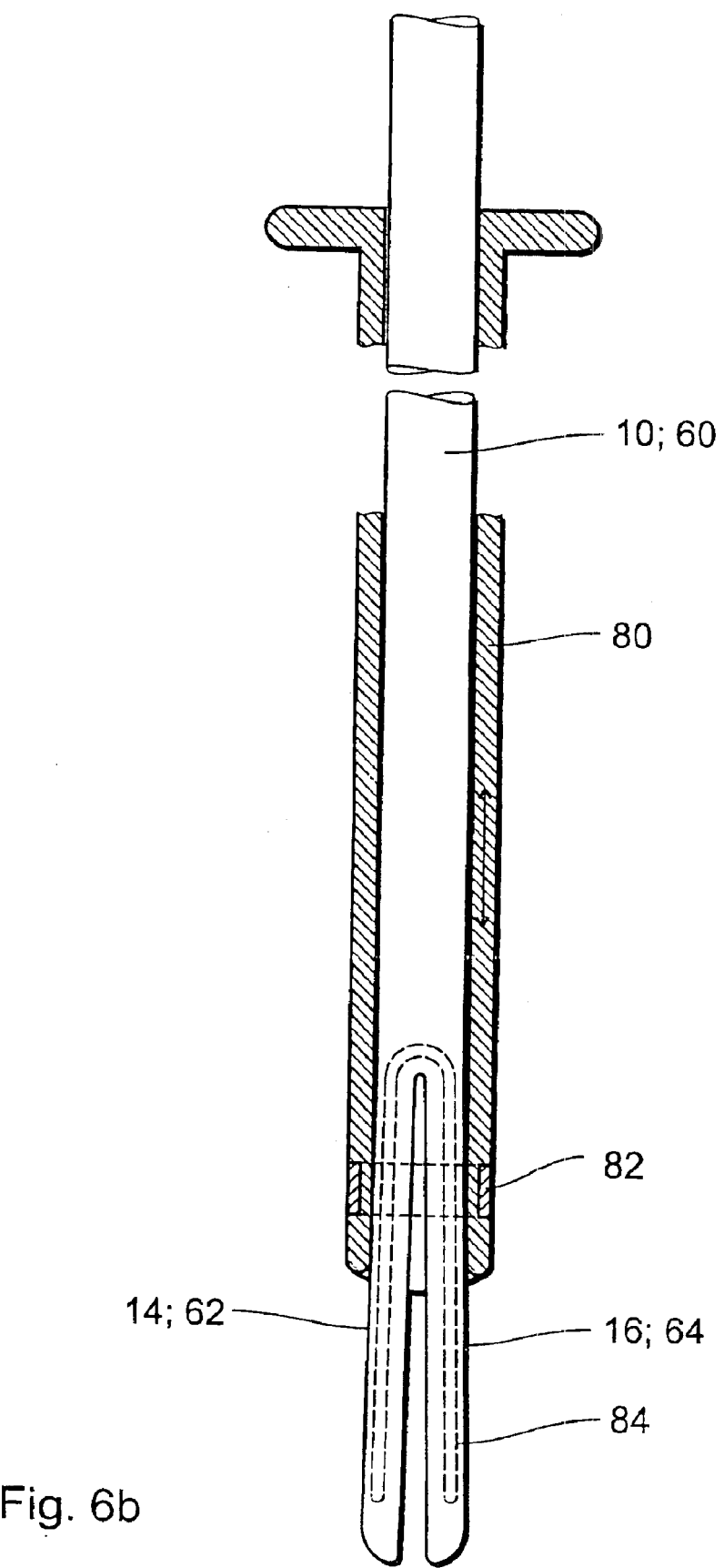

The electrode line shown in FIG. 6b provides 12 ring electrodes 32' placed an the last 5 cm of each branch or hemi-lead 14 and 16, thereby doubling the number of atrial slices to be stimulated compared to the configuration shown in FIGS. 1, 2 and 5a.

Figure 5B:
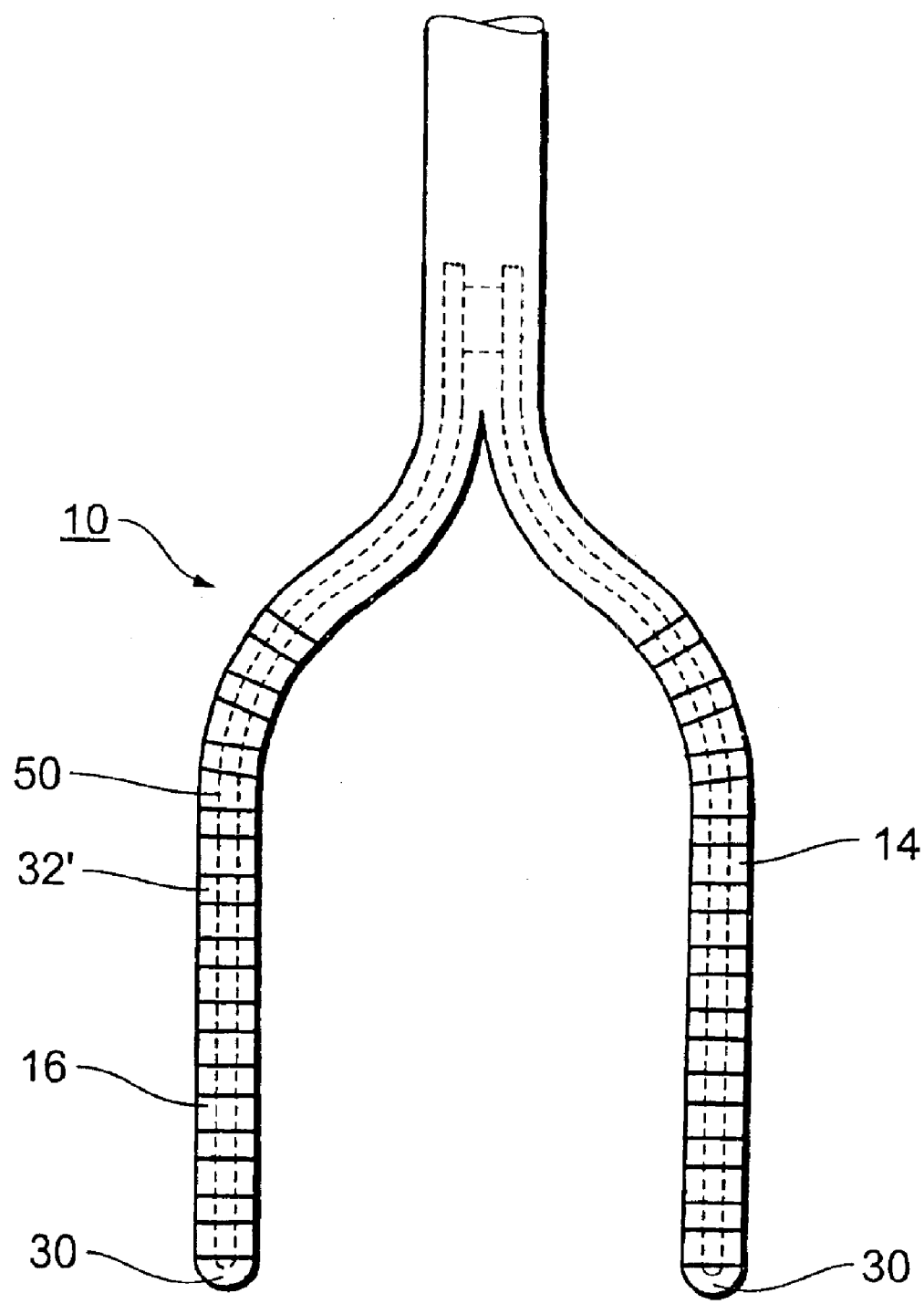
Figure 5C:
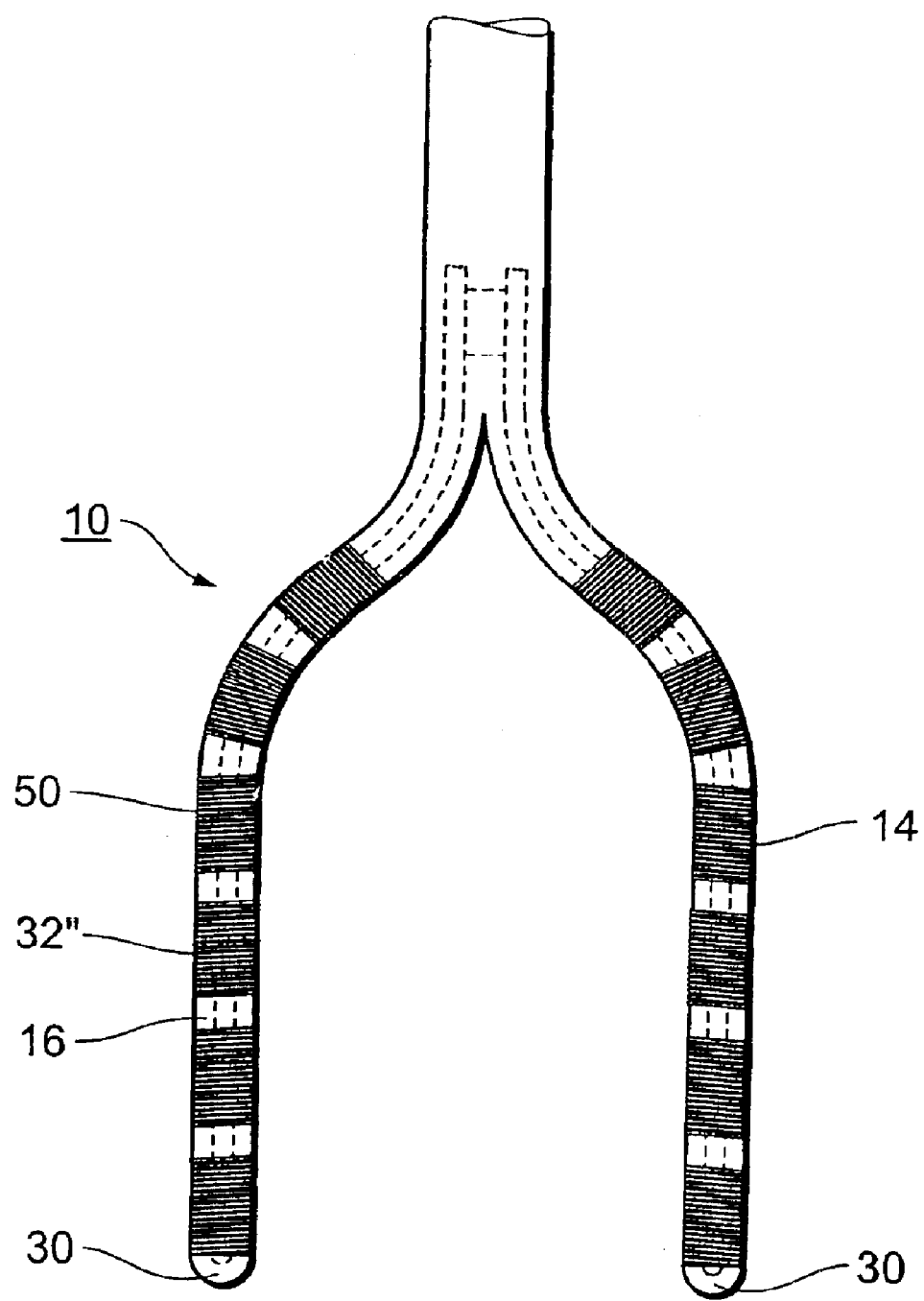

In an alternative embodiment both atrial branches or hemi-leads 14 and 16 bear 6 small diameter coil electrodes 32", each of them 8 mm in length; see FIG. 5c. The electrodes on each branch are separated by insulating plastic transition zones, each zone being 2 mm long.

The electrode configurations for the atrial hemi-leads shown in FIGS. 5b and 5c for an electrode line without ventricular lead could as well be applied to an electrode line having a ventricular lead as shown in FIGS. 1 and 2.

Furthermore, any of the ring electrodes shown in FIGS. 1 to 5 could as well be a split ring electrode, comprising two annular conducting surfaces close to each other separated by a small insulating ring.

So that the distal end of the electrode line 10, 10', 10" or 60 can be introduced by way of the vena cava into the atrium and ventricle of the heart, means are provided which make it possible for the branches 12, 14 and 16 or 62 and 64 to be held close together during the insertion operation, as well as a shaping structure which permit the branches to be split apart after the insertion thereof.

FIGS. 6a and 6b diagrammatically show mechanical means for splitting open the distal end of the electrode line 10 after insertion into a heart. Those mechanical means include a sliding sleeve 80 which may be a catheter guide having a lumen for introduction of an electrode line 10 or 60. Near its distal end the sliding sleeve or catheter guide 80 is provided with a radiologic marker 82 for facilitating the positioning of the catheter guide.

The sliding sleeve 80 is displaceable in the longitudinal direction of the electrode line 10. A shaping structure 84 in the form of a spring element is incorporated in the distal end of electrode line 10 or 60. The spring element 84 is pre-shaped in such a way that, by virtue of spring forces, it causes the electrode-bearing branches 14 and 16 or 62 and 64, respectively, to split apart. During insertion of the electrode line 10 or 60 the sliding sleeve 80 embraces the electrodebearing branches at the distal end of the electrode line 10 or 60 and holds them close together, with the spring structure 84 in a stressed condition. After the insertion step the sliding sleeve 10 is retracted in the longitudinal direction of the electrode line 10 or 60 and releases the electrode-bearing branches. The spring element 84 then causes the individual branches to assume their predetermined shape so that the distal end of the electrode line spreads apart into the individual branches.

Figure 6C:
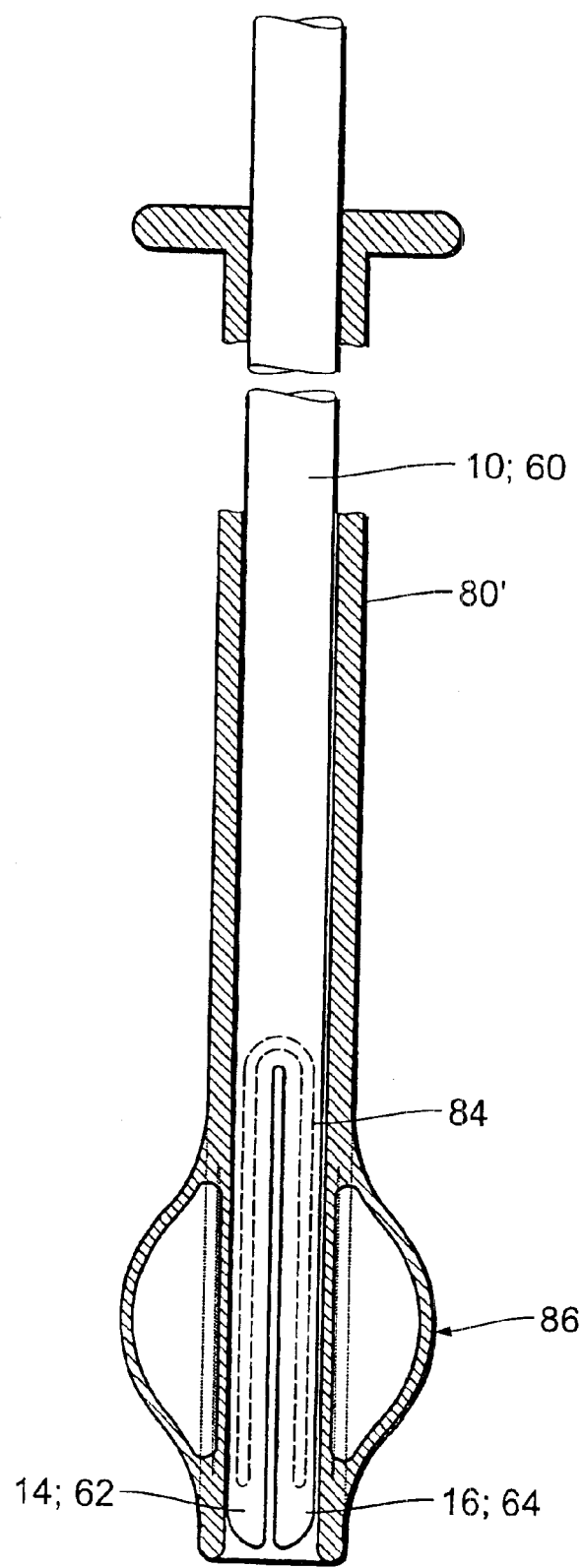

FIG. 6c shows an alternative embodiment of a catheter guide 80' having an inflatable balloon 86 incorporated at or near its distal end. In its inflated state, as shown in FIG. 6c, the balloon 86 has an volume of 1 cm². The balloon 86 may allow for inhibition or reduction of blood flow in the region of the superior vena cava and the right atrium. In addition, means may be provided to inject contrast agent in the distal part of the superior vena cava in order to delineate the border between the superior vena cava and the right atrium by radiologic means. The inhibition or reduction of blood flow prevents the contrast agent from quickly disappear from the region of interest. Thereby the problem is solved to determine where the superior vena cava ends and where the atrium begins. This facilitates the precise positioning of the electrode line.

Furthermore, inflation of the balloon 86 may serve for fixation of the catheter guide 80 in a definite position during insertion of the electrode line. After insertion of the electrode line, the balloon 86 is deflated and the sliding sleeve or catheter guide 80 is completely retracted.

Figure 6D:
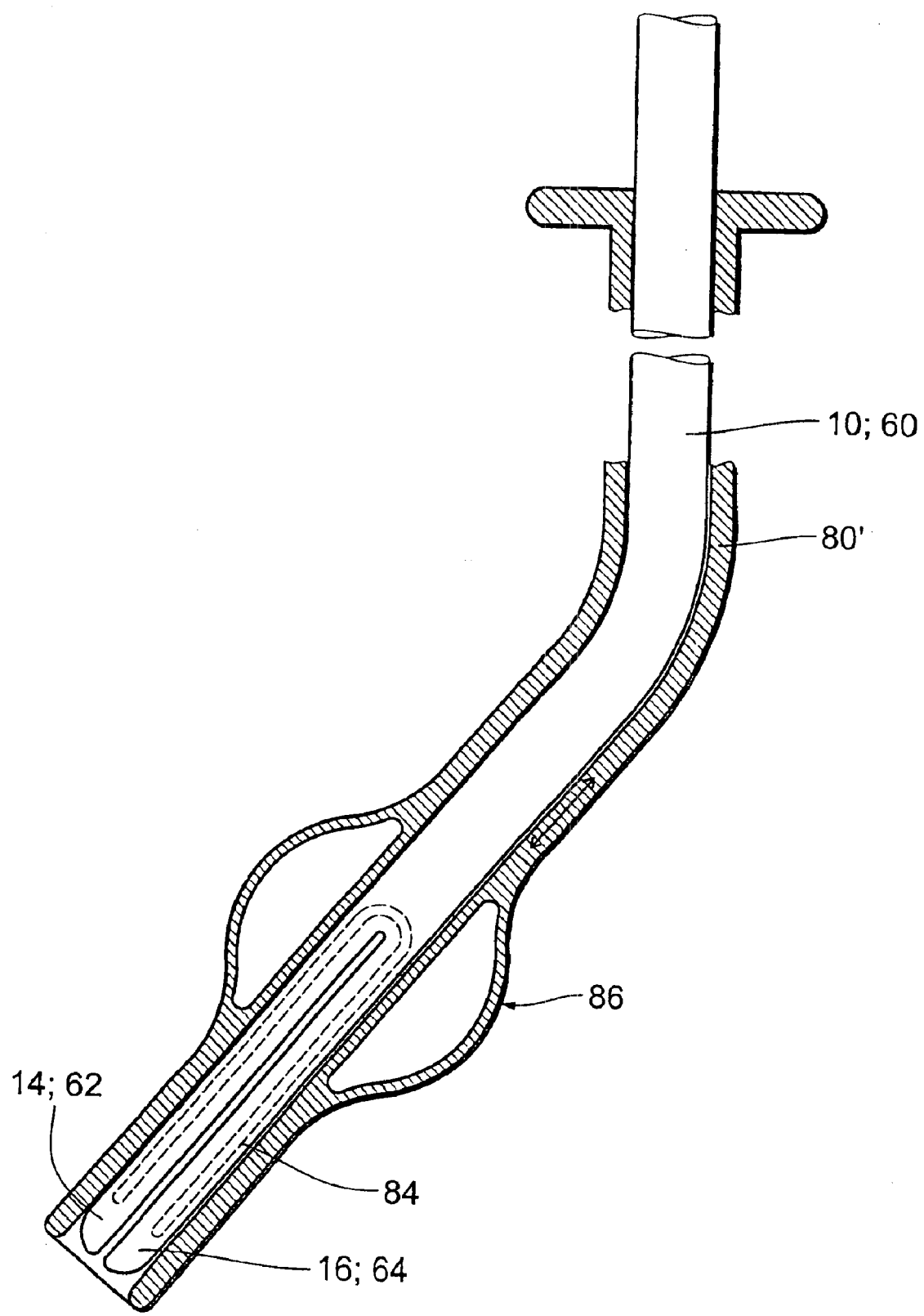

FIG. 6d shows a variation of the embodiment shown in FIG. 6c. The inflatable balloon 86' is placed apart from the distal end of the catheter guide 80'' by 5 mm. The distal 5 mm of the catheter guide are made from soft material like elastic plastic or rubber-like material. Furthermore, in a distance of 2 to 2,5 cm from the distal end, catheter guide 80'' is angulated by approximately 30°. This facilitates the introduction of the catheter into branching vessels like the coronary sinus. Different angles up to 100° may be chosen in accordance to the vessel to be catheterized.

Figure 7:
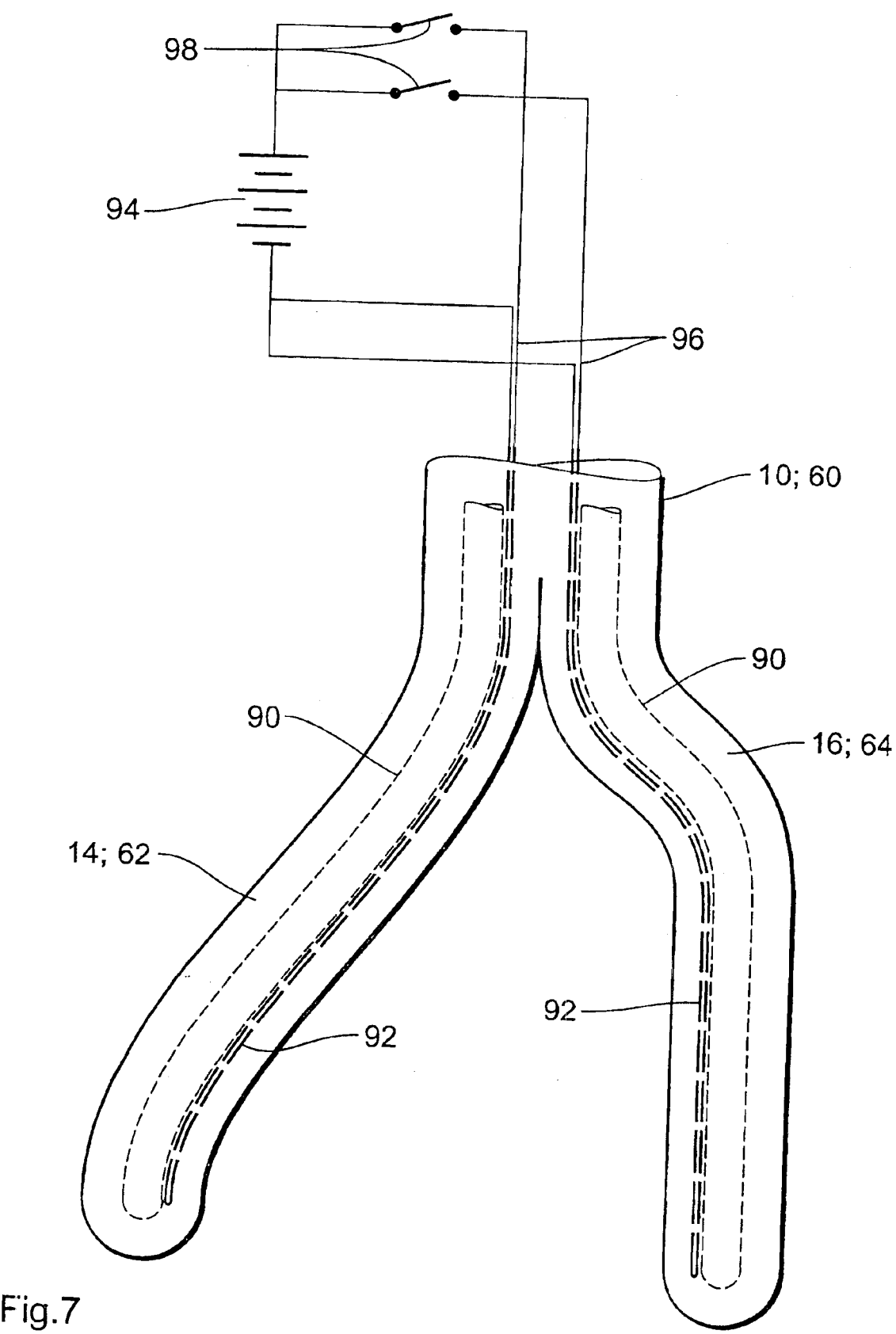

FIG. 7 shows an alternative embodiment of the splitting means and the shaping structure. In the embodiment shown in FIG. 7 the shaping structure 90 comprises a memory metal structure which experiences a change in shape by virtue of being heated above a given temperature. In order to trigger off such a change in shape, provided in the proximity of the memory metal structure 90 are electrical heating elements 92 which are connected to a current source 94 by way of lines 96 provided with switches 98. Closure of the switches 98 can trigger the heating of the electrical heating elements 92 above the temperature required for the abrupt change in shape of the memory metal structure 90.

What is claimed is:

1. An electrode arrangement for the endocardial discharge of defibrillation pulses in one of the atrium and ventricle of the heart, comprising:
   an electrode lead having an undivided proximal end, a distal end and a splitter from which at least two branches of the electrode lead extend to the distal end, each branch having a central core extending from the splitter of the electrode lead; and
   a plurality of electrically conductive surface portions disposed on the at least two branches, said plurality of electrically conductive surface portions for being electrically connected by way of the electrode lead to an electrical pulse-discharging device at the proximal end of the electrode lead, wherein the at least two branches include a septal branch and a lateral branch, and the septal branch and lateral branch each have an equal number of electrically conductive surface portions disposed thereon, and each electrically conductive surface portion of the septal branch is unambiguously associated in pairs with an electrically conductive surface portion of the lateral branch, and
   wherein each pair is actuated in such a way that two electrically conductive surface portions of a pair serve as an anode and a cathode in a bipolar mode of operation and each actuated pair defines a layer spanning from the electrical conductive surface portion of the septal branch to the electrically conductive surface portion of the lateral branch thereby dividing cardiac tissue resulting in a better defibrillation device.

2. The electrode arrangement according to claim 1, further comprising a sliding sleeve displaceable in a longitudinal direction of the electrode lead and actuating means for actuating the sliding sleeve wherein said central core is of one-piece construction in the form of a spring element and causes the branches to split apart when the actuating means moves the sliding sleeve toward the proximal end of the electrode lead.

3. The electrode arrangement according to claim 1, further comprising a sliding sleeve displaceable in a longitudinal direction of the electrode lead, means for actuating the sliding sleeve to split the at least two branches apart, and means for heating the memory member structure so that the shape of the memory member structure can change to maintain good contact between each branch and a wall of the atrium or the ventricle.

4. The electrode arrangement according to claim 3, wherein the memory member structure in at least one of the at least two branches is activatable simultaneously or after the actuating of the sliding sleeve, and a first branch assumes a shape as the septal branch and a second branch assumes a shape as the lateral branch for respectively assuming a septal position and a lateral position in one of the atrium and the ventricle of the heart.

5. The electrode arrangement according to claim 3, wherein at least one memory member structure, in at least one of the branches, experiences a predetermined change in shape by being heated above a predetermined temperature.

6. The electrode arrangement according to claim 5, wherein the memory member structure contains titanium.

7. The electrode arrangement according to claim 1, wherein the electrode lead is split into three different branches.

8. The electrode arrangement according to claim 1, wherein the septal and lateral branch each has disposed thereon about 5 to 7 electrically conductive surface portions.

9. The electrode arrangement according to claim 1, wherein the electrically conductive surface portions are in the form of ring electrodes.

10. The electrode arrangement according to claim 9, wherein at least one of the ring electrodes are formed at the tip or distal end of at least one of the at least two branches.

11. The electrode arrangement according to claim 7, wherein the electrically conductive surface portions of each branch are respectively spaced approximately one centimeter from adjacent electrically conductive surface portions.

12. The electrode arrangement according to claim 7, wherein the at least two branches further includes a ventricular branch which is adapted to assume a position in a ventricle of the heart and has at least one ventricle electrode.

13. The electrode arrangement according to claim 1, wherein said central core is made of a memory member structure that enables good contact to be maintained between each branch and a wall of the atrium of the ventricle.

* * * * *